United States Patent [19]
Nowicky

[11] Patent Number: 5,981,512
[45] Date of Patent: Nov. 9, 1999

[54] MEANS FOR TREATING RADIATION INJURIES

[76] Inventor: Wassyl Nowicky, 7 Margaretenstrasse, A-1040 Vienna, Austria

[21] Appl. No.: 08/981,128
[22] PCT Filed: May 30, 1996
[86] PCT No.: PCT/AT96/00099
 § 371 Date: Mar. 17, 1998
 § 102(e) Date: Mar. 17, 1998
[87] PCT Pub. No.: WO96/38154
 PCT Pub. Date: Dec. 5, 1996

[30] Foreign Application Priority Data

Jun. 1, 1995 [AT] Austria ........................................ 936/95

[51] Int. Cl.$^6$ .................................................. A61K 31/675
[52] U.S. Cl. ................................................................ 514/81
[58] Field of Search ................................................. 514/81

[56] References Cited

U.S. PATENT DOCUMENTS

| | | | |
|---|---|---|---|
| 4,735,945 | 4/1988 | Sakamoto | 514/279 |
| 4,970,212 | 11/1990 | Nowicky | 514/279 |

FOREIGN PATENT DOCUMENTS

| | | |
|---|---|---|
| 354644 | 1/1980 | Austria . |
| 377988 | 5/1985 | Austria . |
| 326627 | 8/1989 | European Pat. Off. . |
| 2366020 | 6/1977 | France . |
| 2110533 | 6/1983 | United Kingdom . |
| 8300486 | 2/1983 | WIPO . |

OTHER PUBLICATIONS

Journal of Cellular Biochemistry, Supplement 11A (1987) UCLA Symposia on Molecular & Cellular Biology. (Abstracts) Nowicky, J.W., "Tumor Progession and Metastasis."p. 101.

Nowicky, J.W., et al. "Evaluation of Clinical Studies of Ukrain in Cancer Patients."Journal of Chemotheraphy, Supp. to N. 4, vol. 3, (1991) pp. 522–524.

Nowicky, J.W., et al. "Evaluation of Thiophosphoric Acid Alkaloid Derivatives from Chelidonium Majus L ("Ukrain") as an Immunostimulant in Patients with Various Carcinomas." Drugs under experimental and clinical Research, No. 1, vol. XVII, (1991) pp. 139–143.

Musianowycz, J. et al. "Clinical Studies of Ukrain in Terminal Cancer Patients (Phase II). "Drugs under experimental and clinical Research, Supp. to vol. XVIII, (1992) pp. 45–50.

Nowicky, J. W., et al. "Ukrain both as an Anti Cancer and Immunoregulatory Agent."Drugs under experimental and clinical Research, Supp. to vol. XVIII, (1992) pp. 51–54.

Jagiello–Wojtowicz, E. et al, "Effect on Single . . . ", Drugs Under Experimental and Clinical Research, vol. 18, 1992, pp. 85–87.

Jagiello–Wojtowicz, E. et al, "Effect on Prolonged . . . ", Drugs Under Experimental and Clinical Research, vol. 18, 1992, pp. 89–91.

Nowicky, J., et al., "Ukrain" *Drugs of the Future*, vol. 20, No. 11, Nov. 1995 pp. 1207–1208.

Hinton, T., "Folias absorption of resuspended 137Cs relative to other pathways of plant contamination" *Journal of Environmental Radioactivity*, vol. 30, No. 1, 1996.

Chem. Abstr. 105,60 797 m (relating to CA 1 191 837) CA 105: 60797m (1986).

S. Simeon et al., Pharmazie 44 (1989) H.9, pp. 593–597, Tab. 1–3.

Hagers Handbuch der pharmazeutischen Praxis, 4 ed., Springer–Verlag, Berlin–Heidelberg–New York, 3. vol. 1972, pp. 835–841) and 6 vol., Part B (1979), pp. 265–269.

Resch, H. et al., "Estimated Long–Term Effect . . . ", Calcif Tissue Int. (1989) 45:209–213.

Resch, H. et al., "Effects of One Year Hormone . . . " Acta Endocinlogica, 1990, 123, 7 sheets.

Kleinrock, Z. et al., "Some Pharmacological Properties . . . " Drugs Under Experimental and Clinical Research, vol. 18, 1992, pp. 93–96.

*Primary Examiner*—Phyllis G. Spivack
*Attorney, Agent, or Firm*—Ladas & Parry

[57] ABSTRACT

There is disclosed the use of phosphorus derivatives of alkaloids of formula (I), as disclosed herein, for the treatment or prevention of radiation injuries.

4 Claims, No Drawings

MEANS FOR TREATING RADIATION INJURIES

This application is PCT application AT96/00099 filed on May 30, 1996 which designated the U.S.

The present invention relates to the use of phosphorus derivatives of alkaloids for the preparation of a medicament for treating radiation injuries.

Austrian patent 377 988 and Austrian patent 354 644 describe methods for the preparation of new phosphorus derivatives of alkaloides and of new salts of alkaloid derivatives of thiophosphoric acid, respectively. Such compounds have a pharmacologic activity and can be used as cytostatic agents.

Compound

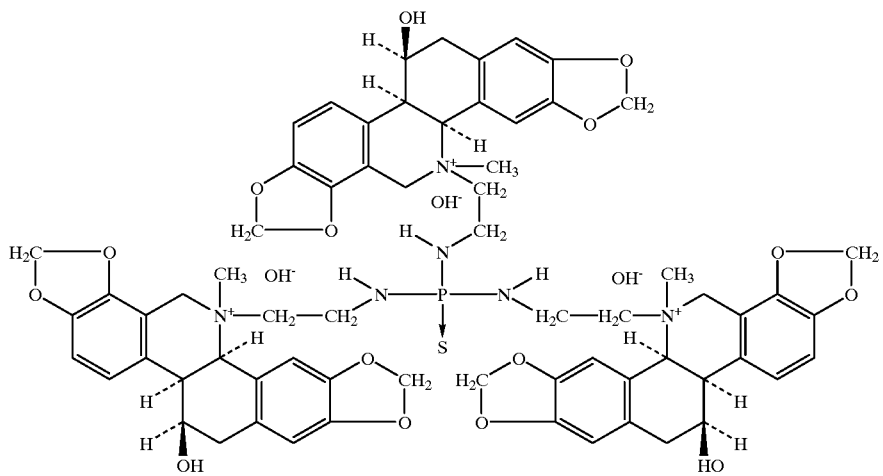

is disclosed in AT 377988 in Example 1.

Surprisingly, it has now been found that the phosphorus derivatives of alkaloids, disclosed in Austrian patent 377 988 and Austrian patent 354 644, respectively, can be used for the preparation of medicaments for the treatment of radiation injuries as well as for the prevention of radiation injuries expected on account of radiation exposures.

Methods for the preparation of phosphorus derivatives of alkaloids of the general formula (I)

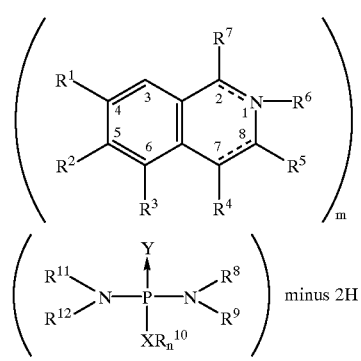

(I)

minus 2H wherein m and n=1, 2 or 3; $R^1$, $R^2$ and $R^3$ are each independently H or methoxy, wherein $R^1$ and $R^2$, or $R^2$ and $R^3$ together also may represent a methylene dioxy group;

$R^4$ and $R^5$, together with the C atoms, to which they are attached, form an optionally totally or partially hydrogenated phenyl or naphthyl group, which in turn may be substituted by methoxy, hydroxy or dioxymethyl, wherein $R^7$ is H or =O or an equal ring system bonded via a —$CH_2$—CO—$CH_2$ chain, $R^6$ is —$CH_3$, and double bonds may be present in positions 1, 2 and/or 7, 8; or $R^6$ and $R^7$ together with the C and N atoms, to which they are attached, form an optionally hydrogenated benzo or naphtho ring system, which in turn may be substituted by methoxy, oxo, methyl or dioxymethyl groups, wherein the C—N bond in positions 1, 2 may be missing, and $R^4$ and $R^5$ are H;

$R^{10}$=2H, —$CH_2$—$CH_2$—, H or —$CH_2$—$CH_2$Cl;

X=O or N;

$R^8+R^9$ and $R^{11}+R^{12}$ are —$CH_2$—$CH_2$— and, if Y=S, X=N and n=2, $R^{11}$ and $R^{12}$ are —$CH_2$—$CH_2$—, —$CH_2$—$CH_2$—O—CH—$_2$— or

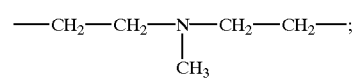

if Y=S, X=N, n=2, $R^2$ and $R^3$ represent —$CH_2$—$CH_2$—,

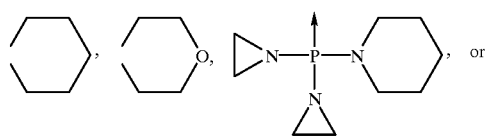

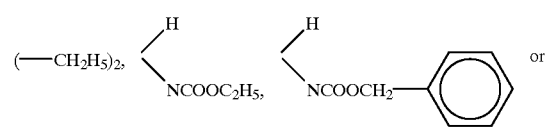

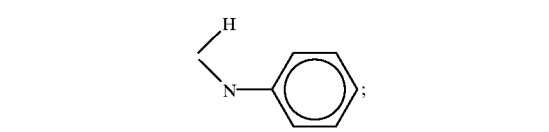

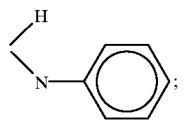

if Y=S, X=O, n=1, R³ is

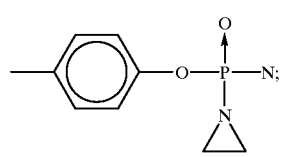

if Y=O, X=N, n=1, R³ is

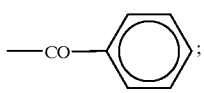

if Y=O, X=N, n=2, R¹¹ and R¹² are

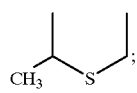

and if Y=O, X=O, n=1,
R¹¹ and R¹² are each —CH₂—CH₂—Cl, R¹⁰ is H₂ and R¹¹+R¹² are —CH₂—CH₂— or —CH₂—CH₂—CH₂—, if Y=S, X=N, R³ is —CH₂—CH₂—, as well as their salts with pharmaceutically compatible acids, are known from Austrian patent 377 988; the preparation of alkaloid derivatives of thiophosphoric acid of the general formula

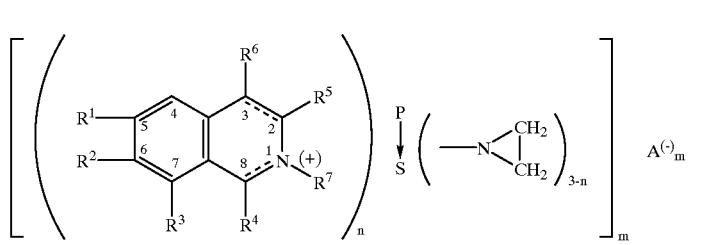

(I)

wherein n is 1, 2 or 3; m represents 1, 2 or 3; R¹, R² and R³ each independently are hydrogen or methoxy, wherein R¹ and R² or R² and R³ together also may represent a methylene dioxy group; R⁴ is hydrogen, hydroxy or methyl; and, if R⁶ is hydrogen, R⁵ and R⁷ together form the group

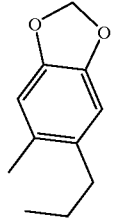

or, if R⁷ represents a methyl group, the groups R⁵ and R⁶ represent the group

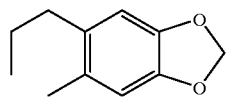

and in positions 1, 8 and/or 2, 3 there may be a double bond; and A is a monovalent or the equivalent portion of a polyvalent anion, is disclosed in Austrian patent 354 644.

According to a particularly preferred embodiment of the present invention, the reaction product of the alkaloids of *Chelidonium maius L.* with thiophosphoric acid triaziridide is used for the preparation of a medicament for the treatment or prevention in case of radiation injuries.

For reasons of simplicity, this reaction product will be named "Ukrain" in the following.

The surprising effect of Ukrain in the treatment or prevention of radiation injuries will be demonstrated in the following by way of a case description.

The following alkaloid components have proved to be especially suitable: coptisin, stylopin, berberin, protopin, allo-kryptopin, spartein, corysamin, chelidimerin, oxysanguinarin, sanguinarin, dihydroxysanuinarin, chelidonin, homochelidonin, methoxychelidonin, chelerythrin, chelilutin, winblastin, colchicin, cholchicein, and desacetyl-N-methyl-colchinin.

The following are particularly useful as phosphorous compounds for the conversion in accordance with the invention:

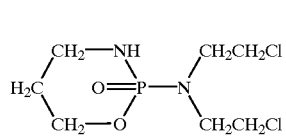
(XXXIX)

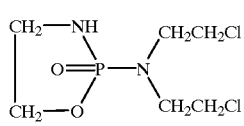
(XL)

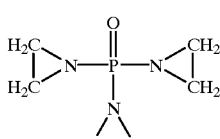
(LIV)

-continued
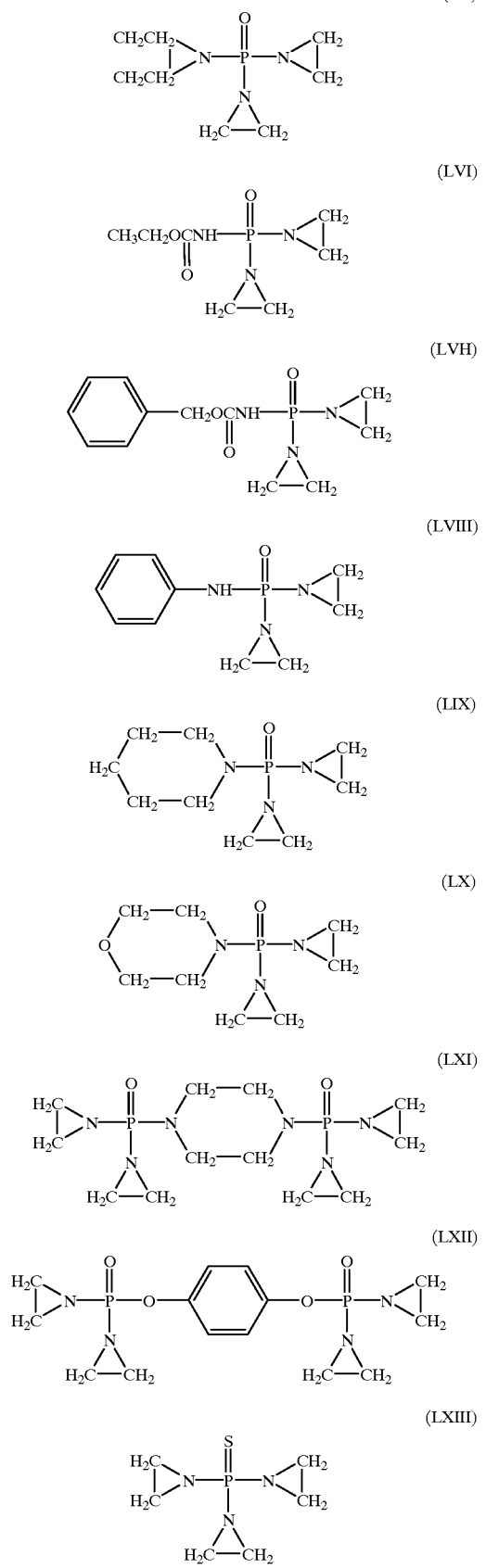
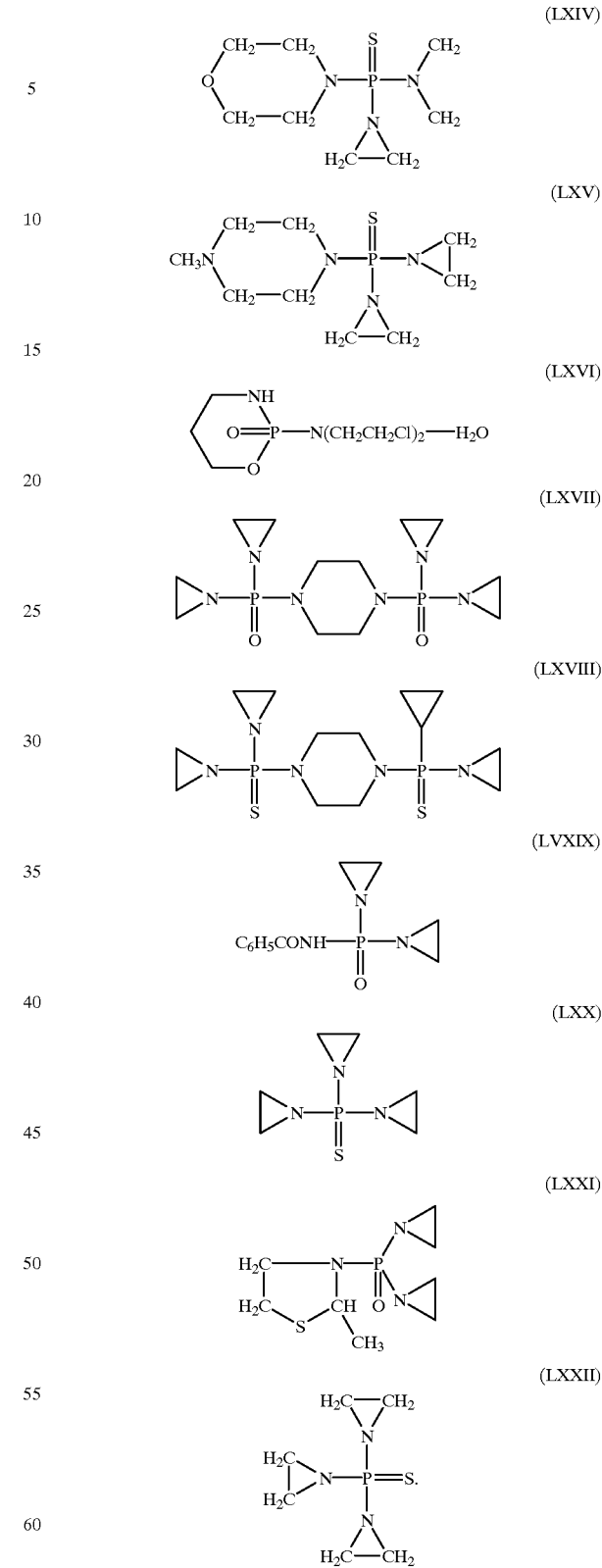
The Chernobyl-Syndrome has been described in the literature several times. Beside an increased cancer and malformation rate in adults, children and people not yet born at that time, syndromes have been reported which indicate a deregulation of the immune system. It has been known that a strong radiation exposure of the organism leads to a variety of similar symptoms.

Description of Cases

1. N.N., female, 8 years old, born in Kiev, 6 months after the reactor accident- Normal birth procedure; retarded general development; slow weight increase despite optimum food supply. Blood count still within the standard, increased blood sedimentation (16/38), ailing. In 1994, a treatment with Ukrain, 5 ml of Ukrain administered orally every third day together with the main meal, 10 times, has been prescribed. Noticeable improvement of the general condition, blood sedimentation within the standard.
2. K.K., male, 11 years old, lives in the vicinity of Kiev. At the age of 3, noticeable deterioration of the general condition. Iodine 131 damage of the thyroid gland is diagnosed, "2nd degree". Toxoplasmosis antibodies in the serum. A therapy somewhat improves his general condition, and the toxoplasmosis antigen titer decreases. Ukrain, 5 ml, orally administered every second day, noticeably improves the patient's general condition, after 2 series of 10 ampoules each, with a pause of 20 days in between. A scintillogram of the thyroid gland shows only little deviation from the standard any more.
3. L.L., male, 7 years old, "post-Chernobyl child"; 2nd degree alteration of the thyroidea, uncontrollable *Giardia lamblia* infection with signs of a general immune deficiency with recurrent commonplace infections. After treatment with 10 times 5 ml of Ukrain, i.m, rapid improvement of the general state of health. After the treatment, the Lambliasis is no longer detectable. Thyroid gland values at the edge of the standard.

The medicaments produced according to the invention preferably consist of an aqueous solution of the utilized alkaloid phosphorus derivatives or the salts thereof, optionally in combination with further auxiliary agents known per se. The administration of the medicament according to the invention is preferably by injection, e.g. intraperitoneally, intramuscularly or intravenously, the dosage varying with the respective case and being correlated with the severity of the illness to be treated as well as with the patient's condition.

It is within the knowledge of the medical doctor treating the patient to determine the suitable dose in each case.

I claim:

1. A method for preventing damage caused by radiation exposure comprising administering to a mammal who will be exposed to radiation or treating damage caused by radiation exposure comprising administering to a patient in need of such treatment an alkaloid derivative of thiophosphoric acid of formula,

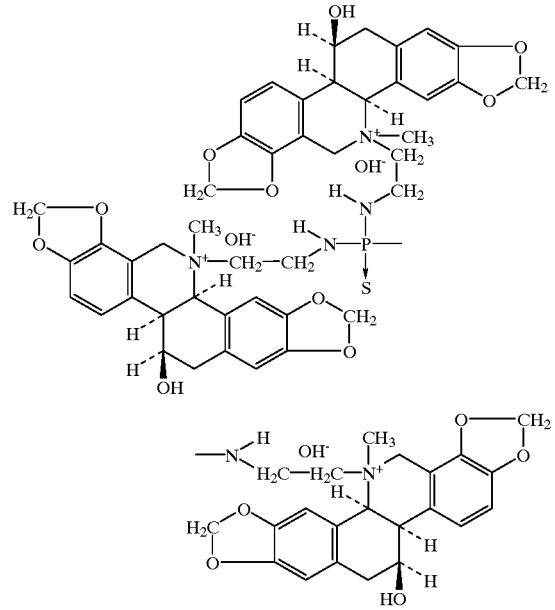

2. A method according to claim 1 wherein the mammal is a human.
3. A method for preventing damage caused by radiation exposure comprising administering to a mammal who will be exposed to radiation or treating damage caused by radiation exposure comprising administering to a patient in need of such treatment the reaction product of the alkaloids of *Chelidonium majus L.* with thiosphosphoric acid triaziridide.
4. A method according to claim 3 wherein the mammal is a human.

* * * * *